Figure 1:
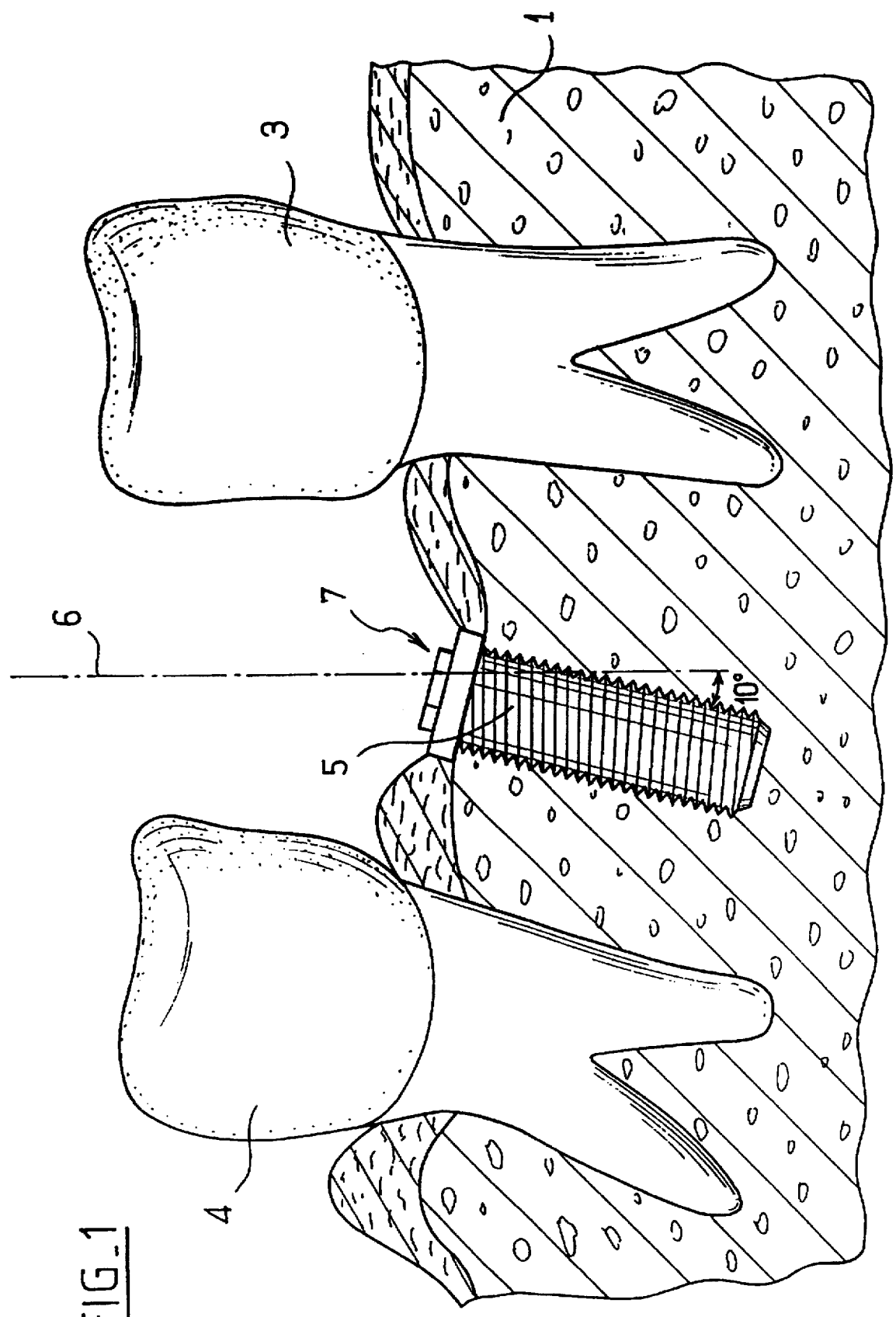

United States Patent [19]
Tyszblat Sadoun

[11] Patent Number: 5,695,337
[45] Date of Patent: Dec. 9, 1997

[54] PROCESS FOR PRODUCING A DENTAL PROSTHESIS SECURED ON AN IMPLANT AND AN INTERMEDIATE PIECE USEABLE FOR IMPLEMENTING THIS PROCESS

[76] Inventor: Michèle Tyszblat Sadoun, 1 Bis, avenue Séverine, 92400 Courbevoie, France

[21] Appl. No.: 539,656

[22] Filed: Oct. 5, 1995

[30] Foreign Application Priority Data

Oct. 5, 1994 [FR] France .................. 94 11899

[51] Int. Cl.$^6$ .................................................. A61C 11/00
[52] U.S. Cl. .................................... 433/213; 433/173
[58] Field of Search ............................. 433/172, 173, 433/174, 175, 213

[56] References Cited

U.S. PATENT DOCUMENTS

| | | | |
|---|---|---|---|
| 4,744,756 | 5/1988 | Ross | 433/173 |
| 5,000,685 | 3/1991 | Brajnovic | 433/173 |
| 5,052,929 | 10/1991 | Seal | 433/173 |
| 5,180,303 | 1/1993 | Homburg et al. | 433/173 |
| 5,316,477 | 5/1994 | Calderon | 433/172 |
| 5,447,435 | 9/1995 | Brodbeck | 433/172 |

FOREIGN PATENT DOCUMENTS

| | | |
|---|---|---|
| 0240643 | 10/1987 | European Pat. Off. . |
| 241384 | 10/1987 | European Pat. Off. . |

*Primary Examiner*—Cary E. O'Connor
*Attorney, Agent, or Firm*—Nixon & Vanderhye, P.C.

[57] ABSTRACT

The present invention provides a process for producing a dental prosthesis secured on an implant and an intermediate piece usable for implementing same.

15 Claims, 4 Drawing Sheets

FIG_1

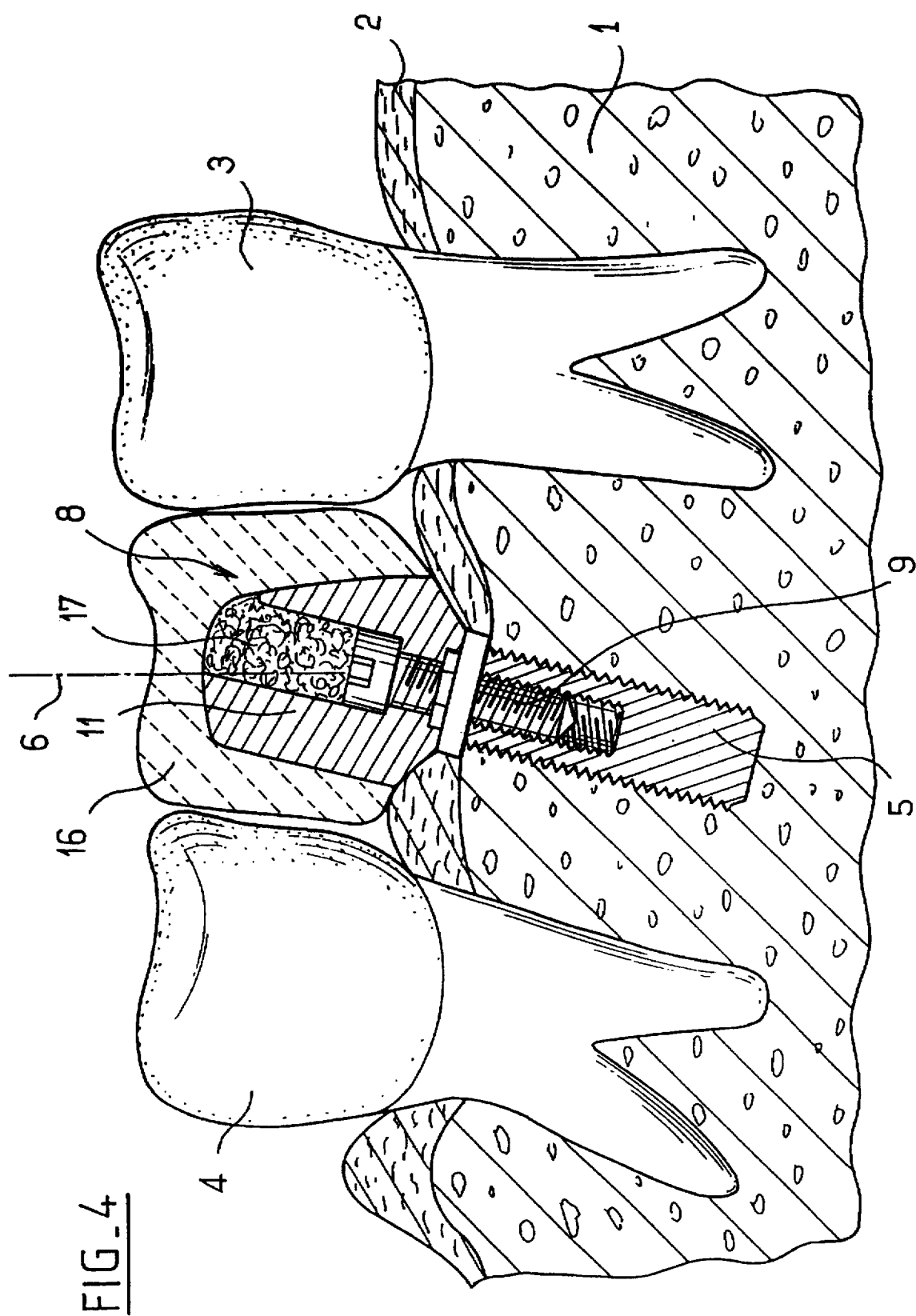
FIG_4

PROCESS FOR PRODUCING A DENTAL PROSTHESIS SECURED ON AN IMPLANT AND AN INTERMEDIATE PIECE USEABLE FOR IMPLEMENTING THIS PROCESS

The present invention relates to a process for producing a dental prosthesis secured on a implant and intermediate piece usable for implementing this process.

In a certain number of cases it is advantageous to replace a natural tooth with a prosthesis which is supported by an implant secured directly in the upper or lower jaw.

Such an implant is, for example, in the form of a cylindrical screw made of titanium which is engaged deeply enough in the jaw in which it is mobilized.

A prosthesis is then secured by screwing onto the implant.

Known processes which make use of this technique present a certain number of difficulties.

First of all, the prosthesis must be firmly attached to the plant, and this involves a very good match between the shape of the upper part of the implant and the shape of the lower part of the prosthesis which fits onto the implant.

It is also necessary that the prosthesis should have a sufficient mechanical strength to withstand the forces to which it is subjected during chewing.

To do this, it is known to employ an industrial intermediate piece made of ceramic which is secured to the implant with the aid of a screw and on which an artificial crown is engaged in the shape of a natural tooth.

However, this solution is not entirely satisfactory because of the fact that the implant, which must be positioned as a function of the configuration of the jaw, can, in some cases, be inclined at a significant angle in relation to the axis of the tooth to be replaced and, in other cases, may be offset sideways in relation to this axis.

In such circumstances, it is difficult, bearing in mind its hardness, to machine the ceramic intermediate piece when it is being placed onto the implant in the patient's mouth or on a model of the patient's mouth.

As a result, with the known devices, the ceramic intermediate piece generally remains on the axis of the implant, and this imposes a very unsymmetrical structure on the crown which is placed over the intermediate piece.

Moreover, a natural baring of the implant frequently takes place, resulting from a recession of the gum, which has the effect of making the lower part of the prosthesis, and in particular the part of the intermediate piece secured directly to the implant, increasingly visible, which is all the more awkward since the ceramic does not have the appearance, and in particular the translucency of natural teeth.

The subject of the present invention is a process which removes all the abovementioned disadvantages and which enables a practitioner easily to give the intermediate piece, placed on the implant in the patient's mouth or on a model of the patient's mouth, an appropriate shape for supporting a crown in good conditions.

In other words, the invention gives the practitioner the possibility, after having placed the intermediate piece on the implant or on a model of the patient's mouth, of working on this intermediate piece to give it a traditional, substantially frustoconical shape with the same ease as if he or she were doing it on a natural tooth stump, or even with greater ease.

The subject of the present invention is a process for producing a dental prosthesis, of the type including the stages consisting in immobilizing a preferably metallic implant in the jaw and in securing an intermediate piece to the said implant, preferably with the aid of a screw, this process being characterized in that an intermediate piece is employed which is obtained by sintering a powder based on metal oxides, which has a porous structure with open pores; that the intermediate piece is fitted onto the implant in the patient's mouth or on a model of the patient's mouth; that, with the aid of a tool such as a cutter, the outer surface of the intermediate piece is given an appropriate shape for producing the prosthesis; that the intermediate piece is dismantled from the implant; that the intermediate piece is impregnated with glass by being placed in contact with this glass in an environment at sufficiently high temperature for the glass to infiltrate in the molten state into the intermediate piece and to occupy all of its pores; and that, after cooling, the intermediate piece is secured onto the implant.

According to a preferred embodiment of the invention the outer surface of the intermediate piece is given a tapered, for example substantially frustoconical, shape suitable for acting as support for a crown obtained by conventional means, this tapered shape being the same as that additionally given to a stump of a natural tooth in order to seal an artificial crown thereon.

According to another embodiment of the invention the outer surface of the intermediate piece is given the shape which it is desired to give to the artificial tooth.

In this case the intermediate piece also acts as a dental crown which is secured directly onto the implant.

In a preferred embodiment of this process the glass impregnation stage is performed at a temperature of between approximately 1080° and 1200° C. over a period of 20 min to 2 hours.

A glass which advantageously has the following composition by weight is employed for this purpose:

| | |
|---|---|
| $SiO_2$ | 13 to 20% |
| $Al_2O_3$ | 10 to 28% |
| $B_2O_3$ | 10 to 18% |
| CaO | 0 to 8% |
| $La_2O_3$ | 20 to 50% |
| $TiO_2$ | 0 to 10% |
| $ZnO_2$ | 0 to 5% |
| Colouring oxides | 0 to 10% |

According to a preferred embodiment of the invention, after having impregnated the intermediate piece with glass in the molten state, the part of the intermediate piece which does not come into direct contact with the implant is covered with an enamel which gives the outer surface of the intermediate piece the appearance, and especially the translucency, of natural teeth.

In this way, when the intermediate piece becomes visible as a result of a recession of the gum, it has the same appearance as the crown which covers it.

It is possible to employ for this purpose a dental porcelain which has an adapted expansion coefficient merely for the purpose of modifying the optical effectiveness of the intermediate piece by giving it the appearance of a natural root, or a bioglass which additionally has the advantages of preserving the gingival epithelium and of releasing a bacteriostatic chemical element, for example fluorine.

In accordance with the invention an intermediate piece is advantageously employed which, before impregnation with glass, has pores whose diameter is between approximately 0.2 and 2 µm, the said pores forming a continuous open network which preferably occupies between approximately 15 and 50% of the total volume of the intermediate piece.

In accordance with the invention it is essential that the intermediate piece which is placed in the patient's mouth or on a model of this mouth in order to be worked upon therein by the practitioner like a natural tooth stump should be sufficiently brittle to be subjected to the action of the various dental instruments, but sufficiently solid to preserve its shape and not to break when it undergoes this treatment.

In particular, the intermediate piece must have a part intended to be secured to the implant which withstands the pressure of a securing screw which passes through it and is screwed into a tapped bore in the implant.

In other words, the mechanical characteristics imposed on the intermediate piece are mutually contradictory, resulting in the difficulty in determining the most appropriate material to impart these two properties of brittleness and of toughness to the intermediate piece.

In accordance with the invention an intermediate piece exhibiting good mechanical characteristics can be obtained in the following manner.

A paste is produced by mixing a powder based on metal oxide with an organic binder, after which this paste is shaped to obtain a piece comprising a lower part whose shape corresponds exactly to the shape of the upper part of the implant which is to receive the intermediate piece, and an upper part whose shape is not determined but which can be advantageously cylindrical, this upper part of the intermediate piece being intended to be wrought by the practitioner in the patient's mouth or on a model of the patient's mouth, for example with the aid of a cutter.

The powder based on metal oxide advantageously has a mean particle size of between 2 and 10 micrometers.

Heating of the piece thus obtained is then undertaken, which first of all causes the removal of the organic binder by calcining and then the sintering of the powder based on metal oxide is undertaken, that is to say the binding of the various powdered particles to one another.

The intermediate piece may, for example, be produced with the aid of a paste which includes between 45 and 70% by volume of powder based on metal oxide and from 30 to 55% by volume of organic binder.

A mixture of alumina ($Al_2O_3$) and of partially stabilized zirconia ($ZrO_2$) is preferably employed as powder based on metal oxide.

The partially stabilized zirconia employed may be a mixture consisting of 88 mol % of zirconium oxide and 12 mol % of cerium oxide, or 90 mol % of zirconium oxide and 10 mol % of cerium oxide, or 98 mol % of zirconium oxide and 2 mol % of yttrium oxide, or 97 mol % of zirconium oxide and 3 mol % of yttrium oxide.

The proportion of alumina and of zirconia in such a powder based on metal oxide is from 0 to 70% by weight of alumina and 30 to 100% by weight of zirconia.

The powder based on metal oxide may be advantageously doped to colour it by introducing into it metal oxides of transition elements such as Ti, V, Cr, Mn, Fe, Co and Ni in a proportion which is preferably between 0 and 1% by weight.

The removal of the binder is advantageously performed by calcining at a temperature of between approximately 280° and 400° C. for a period of 2 to 24 hours, the temperature rise being performed at a rate of approximately 5° to 10° C. per hour.

The sintering is preferably performed at a temperature of between 1100° and 1450° C. for a period of 2 to 10 hours, the temperature rise being performed at a rate of approximately 60° to 300° C. per hour.

Figure 2:
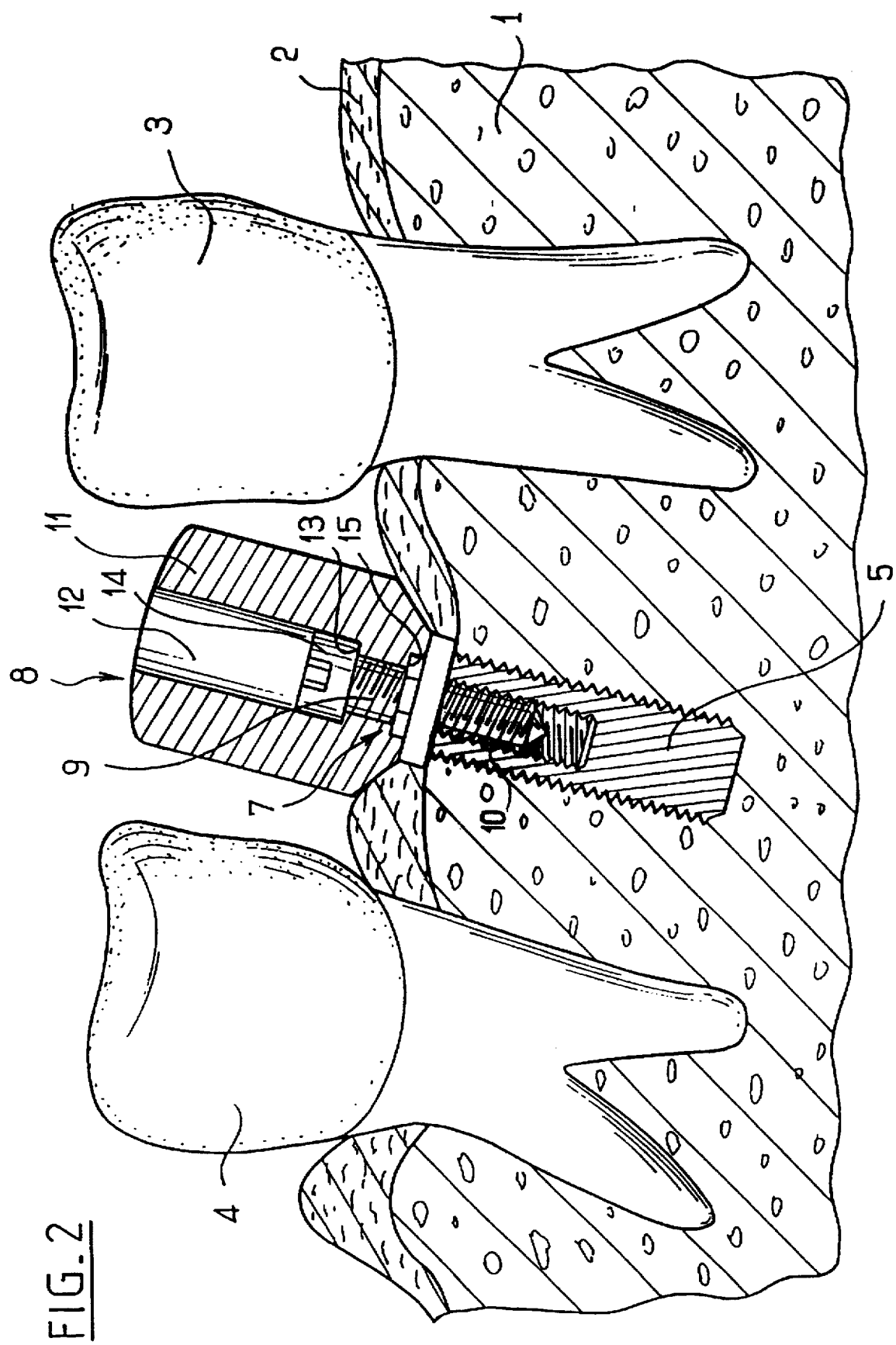
Figure 3:
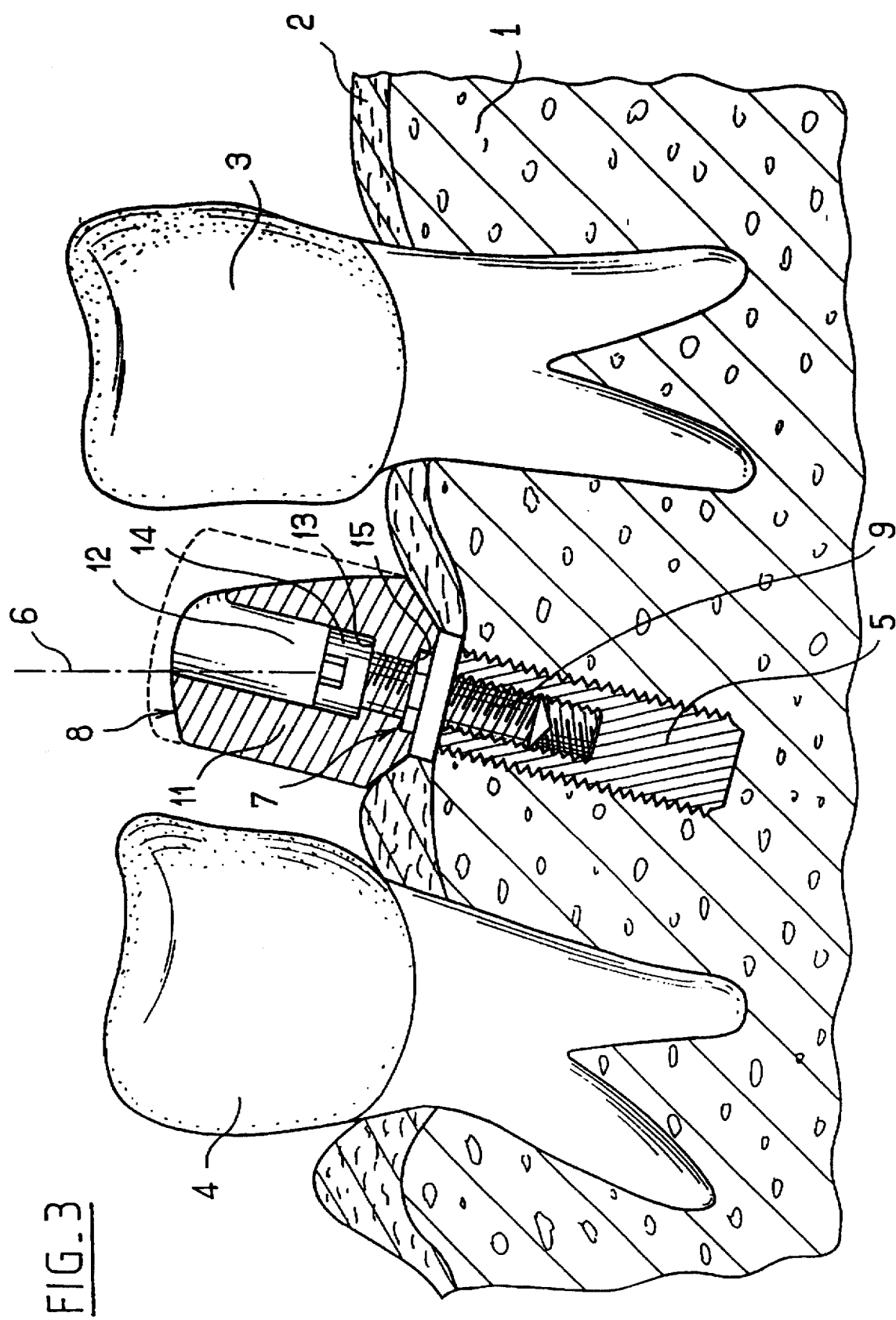

To make the invention better understood, a description will now be given of three examples of embodiment of the process for producing a dental prosthesis according to the invention, with reference to the attached drawing, in which:

FIG. 1 is a sectional view of a portion of jaw in which a metal implant is secured, FIG. 2 is a view similar to that of FIG. 1 after placing in position of a porous intermediate piece made of a sintered powder, FIG. 3 is a view similar to those of the preceding Figures after cutting of the intermediate piece, and FIG. 4 is a view similar to those of the preceding Figures after putting in place of an artificial crown on the cut and glass-impregnated intermediate piece.

A portion of jaw has been shown in the drawing, in which the jaw 1, the gum 2 and two molars 3 and 4 can be seen.

A third molar situated between the other two has been extracted and an implant 5 has been secured in the jaw 1 to support a prosthesis intended to replace this missing tooth.

The implant 5 is a cylindrical screw made of titanium which is screwed directly into the jaw 1.

As can be seen in FIG. 1, the configuration of the jaw is such that it has been impossible to put the implant 5 in place along the axis 6 of the tooth to be replaced.

Consequently, the implant 5 is inclined in relation to this axis 6 at an angle of approximately 10°.

The upper part 7 of the implant 5, which is intended to receive an intermediate piece 8 has an antirotation shape, for example hexagonal, intended to immobilize an intermediate piece which is secured onto the implant 5 only by a screw 9, as shown in FIG. 2.

The intermediate piece 8 comprises a lower part 10, referred to as transgingival part, and an upper part 11, referred to as supragingival part.

The transgingival part 10 of the intermediate piece has a frustoconical shape whereas its supragingival part 11 has a cylindrical shape, preferably of circular or elliptical section.

An orifice 12 passes axially through the intermediate piece 8 and, in the vicinity of the separation between the transgingival 10 and supragingival 11 parts of the intermediate piece, comprises a change in diameter which defines a shoulder 13.

The screw 9 is engaged axially in the orifice 12 passing through the intermediate piece, the head 14 of this screw bearing on the shoulder 13 to tighten the intermediate piece 8 against the implant 5.

The mouth 15 of the passage orifice 12, situated on the side of the implant 5 has a hexagonal shape corresponding exactly to the hexagonal shape of the antirotation part 7 of the implant 5.

The intermediate piece 8, which is secured to the implant 5 is made of a powder based on a metal oxide which, according to the invention, has the required mechanical properties, namely a brittleness and a toughness which are suitably determined.

Thus, the mechanical strength of the porous intermediate piece, before impregnation with glass, can be measured by a three-point flexure test which gives a strength of 40 to 150 MPa.

At the same time, the intermediate piece is sufficiently brittle to be capable of being easily wrought in the patient's mouth or on a model of the patient's mouth with traditional dental instruments.

The piece is corrected by the practitioner to take on a frustoconical shape which can be seen in FIG. 3.

This frustoconical shape is of the same type as that which the practitioner gives to a tooth stump to prepare it to receive an artificial crown.

It can be seen in FIG. 3 that the axis of the frustoconical shape of the intermediate piece coincides appreciably with that 6 of the tooth to be replaced.

In accordance with the invention the intermediate piece is then dismantled from the implant and impregnated with a glass.

It is then enamelled externally in its transgingival part using a bioglass.

Thus repaired, the intermediate piece 8 is secured again onto the implant, its orifice 12 being packed with a filling material 17, to receive a crown 16 as shown in FIG. 4.

It can be seen that, by virtue of the invention, the crown 16 has a shape which is symmetrical in relation to the axis 6 of the replaced tooth, which gives it a great toughness.

Three examples of embodiment of the process for producing a dental prosthesis according to the invention will now be described.

EXAMPLE 1

To produce a middle incisor prosthesis, a powder is prepared based on metal oxide composed of 50% by weight of alumina and 50% by weight of zirconia partially stabilized with 12 mol % of cerium oxide, to which 0.6% by weight of ferrous oxide $Fe_2O_3$ is added, the mean particle size of the pulverulent mixture thus obtained being 10 μm and its specific surface is 1.5 m²/g.

This mixture is incorporated into a thermoplastic organic binder in a weight proportion of 68% of powder per 32% of binder.

The thermoplastic binder has a weight composition of 67% of polystyrene, 23% of paraffin wax and 10% of aluminium stearate.

A paste is thus obtained which is injected into a mould whose cavity defines an intermediate piece with an external diameter of 9 mm.

After the paste has set, the intermediate piece is demoulded and is heated to a temperature of 320° C. at a rate of 8° C. per hour.

This first heating stage results in the calcining of the binder and the formation of the network of pores in the powder based on metal oxide.

The piece is then heated to a temperature of 1400° C. for 5 hours, the heating being performed at a rate of 5° C. per minute.

This second heating stage results in the sintering of the powder based on metal oxide.

An intermediate piece of porous structure in accordance with the invention is then obtained which has a transgingival part corresponding accurately to the shape of the upper part of the implant, with the result that the intermediate piece is capable of being integrally attached to the implant by tightening without any play.

The piece is then put in place on a model of the patient's mouth and then corrected in the traditional manner until its supragingival part has the shape of an incisor taper suitably prepared to receive an artificial crown.

To this end, the external shape and the orientation of the intermediate piece are made compatible with the adjacent and antagonist teeth of the prosthesis.

When the supragingival part of the intermediate piece is suitably prepared the intermediate piece is dismantled from the implant and is impregnated with a coloured glass in the liquid state, the weight composition of which is as follows:

| | |
|---|---|
| $SiO_2$ | 20% |
| $Al_2O_3$ | 20% |

-continued

| | |
|---|---|
| $B_2O_3$ | 18% |
| $Ca_2O_3$ | 30% |
| CaO | 3% |
| $TiO_2$ | 3% |
| Colouring oxides | 6% |

For this purpose, the glass and the intermediate piece are heated for 2 hours to a temperature of 1080° C.

The transgingival part of the intermediate piece is then enamelled using a bioglass of the following weight composition:

| | |
|---|---|
| $SiO_2$ | 31% |
| $Al_2O_3$ | 20% |
| $CaF_2$ | 39% |
| NaF | 8% |
| $AlF_3$ | 12% |

The intermediate piece is then ready; it can again be secured onto the implant in the patient's mouth, to receive a traditional dental crown sealed onto its supragingival part.

EXAMPLE 2

To produce a premolar prosthesis, a powder is prepared based on metal oxide consisting of 100% by weight of zirconia partially stabilized with 2 mol % of yttrium oxide $Y_2O_3$.

The mean particle size of the ceramic powder is 1 μm and its specific surface is 9 m²/g.

This powder is mixed in a proportion of 50% by volume with a thermoplastic organic binder of the following weight composition:

| | |
|---|---|
| Polypropylene | 65% |
| Wax | 22% |
| Stearic acid | 13% |

An injection paste is thus obtained which is injected into a mould of elliptical cross-section, of 8-mm major axis and 6-mm minor axis.

After the paste has set the piece is demoulded and heated to a temperature of 360° C. at a rate of 5° C. per hour, to calcine the binder.

The piece is then heated to a temperature of 1200° C. for two hours at a rate of 1° C. per min, to carry out the sintering of the powder based on metal oxide.

The intermediate piece is then fitted onto the implant in the patient's mouth and its supragingival part is corrected so as to take on the shape of a dental crown.

After this preparation the intermediate piece is withdrawn from the patient's mouth and a coloured glass of the following weight composition:

| | |
|---|---|
| $SiO_2$ | 15% |
| $Al_2O_3$ | 24% |
| $B_2O_3$ | 10% |
| CaO | 5% |
| $La_2O_3$ | 38% |
| $TiO_2$ | 0% |
| $ZnO_2$ | 5% |
| Colouring oxides | 3% | is impregnated into the porous structure at a temperature of 1180° C. for 20 min.

The transgingival part of the intermediate piece is then enamelled with a coloured conventional dental ceramic, while the supragingival part of the intermediate piece is enamelled in bulk with a dental ceramic of matching expansion coefficient, to form the crown of the prosthesis directly.

EXAMPLE 3

To produce a lateral incisor prosthesis a powder is prepared based on metal oxide consisting of 30% by weight of zirconia $ZrO_2$ partially stabilized with 10 mol % of cerium oxide $CeO_2$, and 70% by weight of alumina $Al_2O_3$, this powder being doped with 0.2% by weight of manganese oxide, 0.2% by weight of titanium oxide and 0.005% by weight of cobalt oxide.

The mean particle size of the powder is 5 μm and its specific surface 5 $m^2/g$.

The powder is mixed, in a proportion of 62% by volume, with a heat-curable organic binder constituting the remaining 38% by volume.

The heat-curable binder consists of 55% by weight of epoxy resin, 22% by weight of reactive diluent, 11% by weight of catalyst, 2% by weight of setting accelerator and 10% by weight of plasticizer.

The injection paste thus prepared is injected into a mould, whose cavity has a cylindrical genera shape 6 mm in diameter.

After demoulding, the piece is heated to a temperature of 400° C. at a rate of 10° C. per hour to carry out the calcining of the binder, then to a temperature of 1300° C. for 6 hours, at a rate of 3° C. per minute, to carry out the sintering of the powder based on metal oxide.

The piece is then fitted onto the implant on a model of the patient's mouth and its supragingival part is wrought to receive a crown.

After preparation and withdrawal from the patient's mouth, the intermediate piece is impregnated with a glass which has the following weight composition:

|                  |      |
|------------------|------|
| $SiO_2$          | 17%  |
| $Al_2O_3$        | 21%  |
| $B_2O_3$         | 13%  |
| CaO              | 0%   |
| $La_2O_3$        | 45%  |
| $ZnO_2$          | 3%   |
| $TiO_2$          | 1%   |
| Colouring oxides | 0%.  |

The impregnation temperature is 1140° C., the treatment time is 1 hour 30 min.

After impregnation, the transgingival part of the intermediate piece is polished very finely.

The piece is then secured to the implant and a crown is sealed onto its supragingival part.

It is obvious that the examples of embodiment which have just been described do not imply any limitation and that they can receive any desirable modification without departing thereby from the scope of the invention.

I claim:

1. A process for producing a dental prosthesis, of the type including a stage consisting of securing an intermediate piece to an implant immobilized in a patient's jaw, wherein an intermediate piece (8) is employed which is obtained by sintering a powder based on metal oxides which has a porous structure with open pores; the intermediate piece (8) is fitted onto the implant (5) in the patient's mouth or on a model of the patient's mouth; with the aid of a tool, the outer surface of the intermediate piece (8) is given an appropriate shape for producing the prosthesis; the intermediate piece is dismantled from the implant (5) the intermediate piece is impregnated with glass by being placed in contact with this glass in an environment at sufficiently high temperature for the glass to infiltrate in the molten state into the intermediate piece and to occupy all of its pores; and after cooling, the intermediate piece (8) is secured again onto the implant (5).

2. A process according to claim 1, wherein the outer surface of the intermediate piece (8) is given a tapered shape suitable for acting as support for a crown (16).

3. A process according to claim 1, wherein the outer surface of the intermediate piece (8) is given the shape which it is desired to give to the artificial tooth.

4. A process according to claim 1, wherein the glass impregnation stage is performed at a temperature of between 1080° and 1200° C. over a period of 20 min to 2 hours.

5. A process according to claim 1, wherein a glass which has the following composition is employed:

|                  |           |
|------------------|-----------|
| $SiO_2$          | 13 to 20% |
| $Al_2O_3$        | 10 to 28% |
| $B_2O_3$         | 10 to 18% |
| CaO              | 0 to 8%   |
| $La_2O_3$        | 20 to 50% |
| $TiO_2$          | 0 to 10%  |
| $ZnO_2$          | 0 to 5%   |
| Colouring oxides | 0 to 10%  |

6. A process according to claim 1, wherein, after having impregnated the intermediate piece (8) with glass in the molten state, the part of the intermediate piece (8) which does not come into direct contact with the implant (5) is covered with an enamel which gives the outer surface of the intermediate piece (8) the appearance, and the translucency, of a natural tooth.

7. An intermediate piece for implementing the process according to claim 1, having, before impregnation with glass, pores whose diameter is between approximately 0.2 and 2 μm, the said pores forming a continuous open network which occupies between approximately 15 and 50% of the total volume of the intermediate piece.

8. A process for manufacturing an intermediate piece according to claim 7, wherein a paste is produced by mixing a powder based on metal oxide with an organic binder; this paste is shaped to obtain a piece comprising a lower part (10) whose shape corresponds exactly to the shape of an upper part (7) of the implant (5) which is to receive the intermediate piece (8), and an upper part (11) whose shape is not determined but which can be advantageously cylindrical, this upper part (11) of the intermediate piece (8) being intended to be wrought by the practitioner in the patient's mouth or on a model of the patient's mouth heating of the piece thus obtained is then undertaken, which first of all causes the removal of the organic binder by calcining and then the sintering of the powder based on metal oxide.

9. A process according to claim 8, wherein the paste is produced by mixing between 45 and 70% by volume of powder based on metal oxide and from 30 to 55% by volume of organic binder.

10. A process according to claim 9, wherein a mixture of alumina ($Al_2O_3$) and of partially stabilized zirconia ($ZrO_2$) is employed as powder base on metal oxide.

11. A process according to claim 10, wherein the proportion of alumina and of zirconia is from 0 to 70% by weight of alumina and 30 to 100% by weight of zirconia.

12. A process according to claim 8, wherein the powder based on metal oxide is doped to colour said powder by introducing into said powder at least one metal oxide of a transition element selected from the group consisting of Ti, V, Cr, Mn, Fe, Co and Ni.

13. The process according to claim 12, wherein said at least one metal oxide is added in a proportion of between 0 and 1% by weight.

14. A process according to claim 8, wherein the removal of the binder is performed by calcining at a temperature of between approximately 280° and 400° C. for a period of 2 to 24 hours, the temperature rise being performed at a rat of approximately 5 to 10° C. per hour.

15. A process according to claim 8, wherein the sintering is performed at a temperature of between 1100° and 1450° C. for a period of 2 to 10 hours, the temperature rise being performed at a rate of approximately 60° to 300° C. per hour.

* * * * *